Aug. 20, 1935. J H NICOLAS Plant Pat. 136
ROSE
Filed March 28, 1935
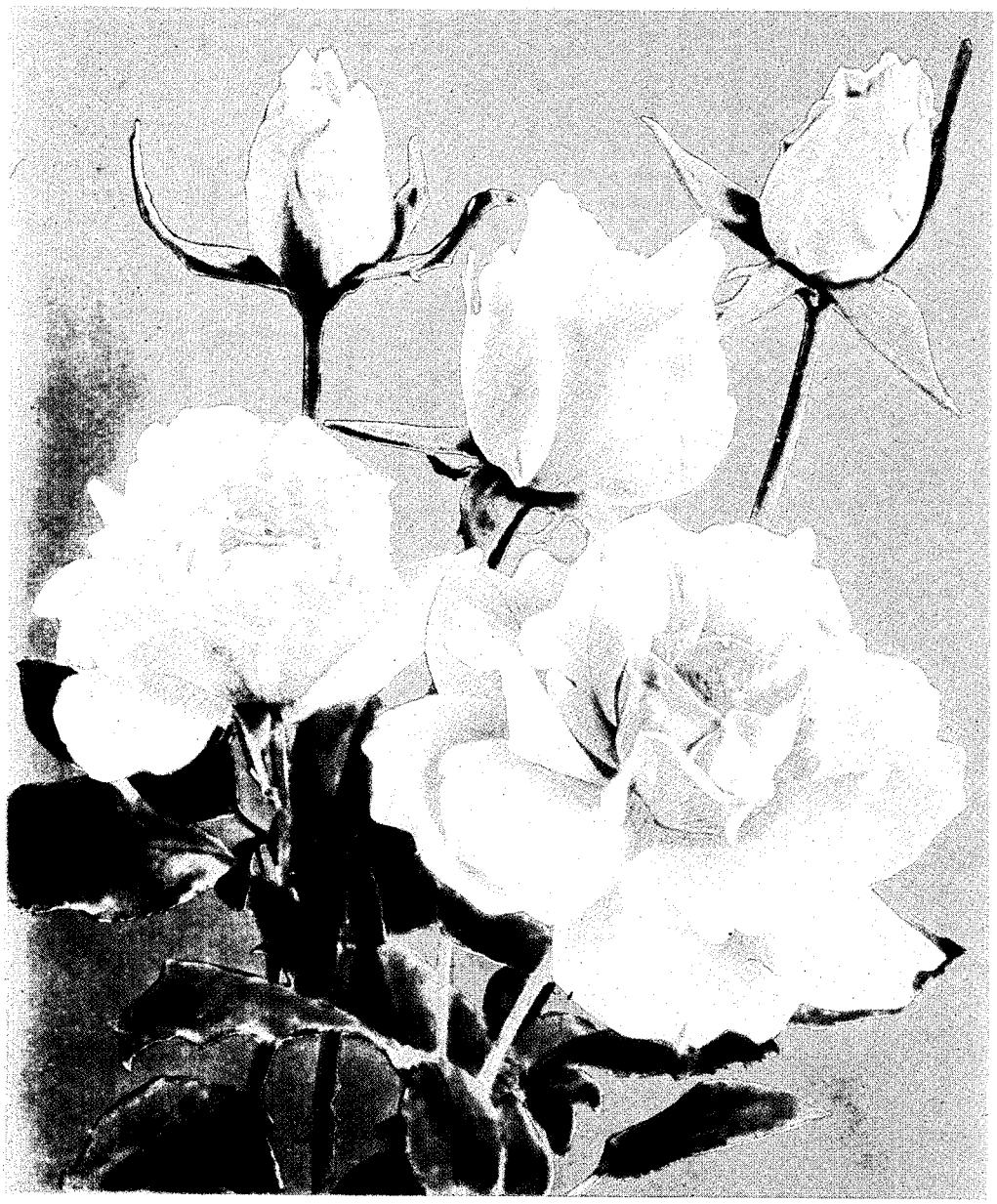
Inventor
J. H. Nicolas
By Robb & Robb
Attorneys Patented Aug. 20, 1935

UNITED STATES PATENT OFFICE

136

ROSE

Jean H. Nicolas, Newark, N. Y., assignor to
Jackson & Perkins Company, Newark, N. Y.

Application March 28, 1935, Serial No. 13,558

1 Claim. (Cl. 47—61)

The present invention relates to a new and distinct variety of rose plant adapted particularly to serve as a bedding rose for mass planting because of its extraordinary brilliance of color and its habit of compact growth.

The primary features of this new rose, produced by the crossing of the two well known varieties "Chas. P. Kilham" and "Mrs. Pierre S. du Pont", reside in the novelty of its color and the extremely prolific flowering habit.

In color, this rose is a cheerful orange flame in the bud, gradually moving to coral and finishing coral with a suffusion of salmon, the informal arrangement of the petals adding materially to the distinction and gay appearance.

The flowering habit of my new variety is in tenure with the color,—a continuous producer which gives to the garden an interrupted note of pleasing, exhilarating color.

The plant is medium dwarf and compact, putting its energy into flowers instead of wood.

Asexual reproduction proves the foregoing characteristics to be permanently fixed.

The following is a detailed description of this new variety:

Parentage:
Seedling.
*Seed parent.*—Chas. P. Kilham.
*Pollen parent.*—Mrs. Pierre S. du Pont.

Classification:
*Botanic.*—Pernetiana Hybrid.
*Commercial.*—Hybrid Tea.

*Flower*

Blooming habit: Continuous.
Other habit: Tremendously floriferous.

Bud:
*Size.*—Large.
*Form.*—Long, pointed. Unaffected by wet and hot weather.
*Color.*—(Gravereaux color system.) When sepals first divide—orange scarlet. When petals begin to unfurl—orange flame. When half blown: inside of petals orange flame, reverse of petals orange flame with yellow suffusion.
*Sepals.*—Smooth edged or branched; curl back when bloom is half open.
*Calyx.*—Shape—pear. Size—small. Aspect—smooth. Odor when rubbed—none.
*Peduncle.*—Length—medium.
*Aspect.*—Smooth.
*Color.*—Medium green.
*Strength.*—Erect, weak, slender.
*Opening.*—Bud opens well.
Unaffected by adverse conditions.

Bloom:
*Size.*—Large. Average size when fully expanded 4″.
*Borne.*—Singly or several together.
*Stems.*—Medium, normal strength.
*Form.*—When first open—cupped. Permanence—flattens.
*Petalage.*—Semi-single (two rows of petals) or double (full but open center). Number of petals under normal conditions varies from 12 to 18.
*Color.*—Center of flower orange flame. Outer petals slightly paler than center; base of petals (aiglet) yellow; inside of petals orange flame; reverse of petals orange coral; general tonality from a distance orange flame.
*Variegations.*—None.
*Discoloration.*—General tonality at end of first day orange flame; second day brilliant coral; third day coral pink.

Petals:
*Texture.*—Thick; unaffected by wet or hot weather.
*Appearance.*—Inside—shiny. Outside—satiny.
*Form.*—Irregularly scalloped.
*Arrangement.*—Informal (with "rags" in center). Petaloids in center—few, large.
*Persistence.*—Drop off cleanly.
*Fragrance.*—Slight. Nature—sweet briar.
*Lasting quality.*—On the plant long; as cut flower very long.

Genital organs:
*Stamens, anthers.*—Large, many. Color—yellow. Arrangement—regular around styles.
*Stamens, filaments (threads).*—Long. Color—white.
*Pollen.*—Lemon yellow.
*Styles.*—Bunched, even length, medium length, heavy.
*Stigmas.*—Color—white.
*Ovaries.*—All enclosed in calyx.

Fruit:
Variety is generally sterile with any pollen.

*Plant*

Form:
Bush.

Growth:
Medium.

Foliage:
Generally 5 leaflets, but sometimes 7.
*Size.*—Large.

*Quantity.*—Abundant.

*Color.*—New foliage—upper side light green; under side pale green. Old foliage—upper side normal green; under side pale green.

*Shape.*—Oval.

*Texture.*—Upper side glossy; under side smooth.

*Ribs and veins.*—Ordinary.

*Edge.*—Serrated (saw toothed).

*Serration.*—Single, sharp.

*Leaf stem.*—Color—green; underside prickles.

*Stipules.*—Medium. Smooth.

*Disease resistance.*—Resistant.

Wood:

*New wood.*—Color—light green. Bark—smooth.

*Old wood.*—Color—green. Bark—smooth.

Thorns (divided into thorns, prickles and short needles):

*Thorns.*—Quantity—On main stalks from base ordinary. On laterals from stalks few. Form—broad base, medium length; hooked downward. Color when young—red. Position—irregular.

*Prickles.*—Quantity—on main stalks none; on laterals none.

*Short needles.*—Quantity—on main stalks none; on laterals none.

I claim:

A new and distinct variety of hybrid tea rose plant for bedding purposes, characterized by its extremely floriferous habit, in combination with its bloom color changing in development from scarlet-orange to coral and then coral suffused with salmon, substantially as shown and described.

JEAN H. NICOLAS.